United States Patent [19]
Kameshima

[11] Patent Number: 5,196,700
[45] Date of Patent: Mar. 23, 1993

[54] ION SOURCE OF MASS SPECTROMETER

[75] Inventor: Norio Kameshima, Kyoto, Japan

[73] Assignee: Shimadzu Corporation, Kyoto, Japan

[21] Appl. No.: 798,755

[22] Filed: Nov. 27, 1991

[30] Foreign Application Priority Data

Nov. 30, 1990 [JP] Japan .................................. 2-338668

[51] Int. Cl.[5] ............................................. H01J 49/04
[52] U.S. Cl. .................................. 250/288; 250/281; 250/423 R
[58] Field of Search ................ 250/288 R, 288 A, 281, 250/282, 423 R

[56] References Cited

U.S. PATENT DOCUMENTS

| | | | |
|---|---|---|---|
| 4,647,772 | 3/1987 | Lewis et al. | 250/288 A |
| 4,960,992 | 10/1990 | Vestal et al. | 250/288 |
| 4,977,785 | 12/1990 | Willoughby et al. | 250/288 |
| 4,996,424 | 2/1991 | Mimura et al. | 250/288 A |
| 5,051,583 | 9/1991 | Mimura et al. | 250/281 |
| 5,103,093 | 4/1992 | Sakairi et al. | 250/288 |

Primary Examiner—Constantine Hannaher
Assistant Examiner—Kiet T. Nguyen

[57] ABSTRACT

An ionization chamber is separated from an ion lens system while the chamber is in contact with an interface block so that they are directly coupled in which a heater embedded in the interface block serves to heat both the interface block and the ionization chamber.

4 Claims, 4 Drawing Sheets

ION SOURCE OF MASS SPECTROMETER

BACKGROUND OF THE INVENTION

1. Field of the Invention

The present invention relates to an ion source section of a mass spectrometer for ionizing a gaseous sample introduced therein.

2. Description of the Prior Art

A gas chromatograph (GC) is provided for separating a gaseous mixture into its various constituent parts. A mass spectrometer (MS) is provided for analyzing a gaseous sample to determine its molecular structure. If the output of a gas chromatograph is coupled to the input of a mass spectrometer, the combined instrument is known as a gas chromatograph/mass spectrometer (GC/MS).

FIG. 3, for example shows a conventional ion source section of a mass spectrometer coupled to a gas chromatograph. The ion source section comprises an ionization chamber 1, an ion extraction electrode 2, an ion lens system 3, and a quadrupole electrode 4 for a quadrupole mass spectrometer. A sample gas is introduced into the ionization chamber 1, vertically to the plane of the drawing, through a sample introduction inlet 1$b$. A filament 1$f$ is provided outside the ionization chamber 1 for injecting electrons into the ionization chamber 1 through an electron injection aperture 1$e$ so that the sample molecule is ionized within the ionization chamber 1. An electron trap 1$t$ is provided for capturing electrons passing through the ionization chamber 1.

FIG. 4 is a rear side of the apparatus of FIG. 3, showing a heater 5 embedded within the ionization chamber 1 for maintaining the sample gas introduced into the chamber 1 at a predetermined temperature. A column 6 for the gas chromatograph is coupled to the ionization chamber 1 through an interface block 7. The interface block 7 is a metal block attached to an outer housing 8 of the mass spectrometer. An introduction aperture 7$h$ coupled to the column 6 of the gas chromatograph passes through the interface block 7. A heater 9 is embedded within the interface block 7. A temperature sensor 10 is provided for generating a control signal to keep the interface block 7 at a predetermined temperature. Because the ionization chamber 1 injects ion to the mass spectrometer portion, which is grounded, the chamber 1 should have a voltage different from the ground. Therefore, it is necessary to electrically isolate the ionization chamber 1 and the interface block 7 when introducing the gas. For this purpose, an isolator 11 having a throughhole is interposed between the interface block 7 and the ionization chamber 1.

The above-structured ion source section of the mass spectrometer has the following problems. Since the sample molecules are attached to the inside wall of the ionization chamber 1 so that the resultant mass spectra may make a ghost, it is necessary to clean the inside of the ionization chamber 1 some times. However, the ionization chamber 1 is secured to with the ion lens system 3 by a bolt 3$b$. So, in order to remove the ionization chamber 1, the ion lens system 3 must be dismantled and it is very troublesome to reassemble the ionization chamber after cleaning. It is preferred that the ionization chamber 1 and the interface block 7 be kept at the same temperature. The isolator 11 which is interposed between them, has a low thermal conductivity. It is, therefore, impossible to heat the ionization chamber 1 by the conducting heat from the interface block 7. A heater must be provided individually in both the interface block 7 and the ionization chamber 1, and therefore is rather difficult to continuously keep them at the same temperature. For this reason, further, the ionization chamber 1 is difficult to be disassembled and reassembled for cleaning.

SUMMARY OF THE INVENTION

To resolve the above problem, it is an object of the present invention to provide an improved ion source of a mass spectrometer suitable for cleaning and heating the ion source.

Briefly described, in accordance with the present invention, an ionization chamber is separated from an ion lens system while the ionization chamber is in contact with an interference block so that they are directly coupled in which a heater embedded in the interface block functions to heat both the interface block and the ionization chamber.

With the arrangement of the present invention, since the ionization chamber is separated from the ion lens system and is directly coupled to the interface block, the ionization chamber can be removed without disassembling the ion lens system. It becomes easier to remove and reassemble the ionization chamber for cleaning it. The interface block and the ionization chamber are directly coupled without any isolator therebetween, and thermal conductivity therebetween is extremely so good that the heater in the interface block is sufficient to heat them both at the same temperature.

Temperature control is very simple.

BRIEF DESCRIPTION OF THE DRAWINGS

The present invention will become more fully understood from the detailed description given hereinbelow and the accompanying drawings which are given by way of illustration only, and thus are not limitative of the present invention and wherein.

DESCRIPTION OF THE PREFERRED EMBODIMENT

Figure 1:
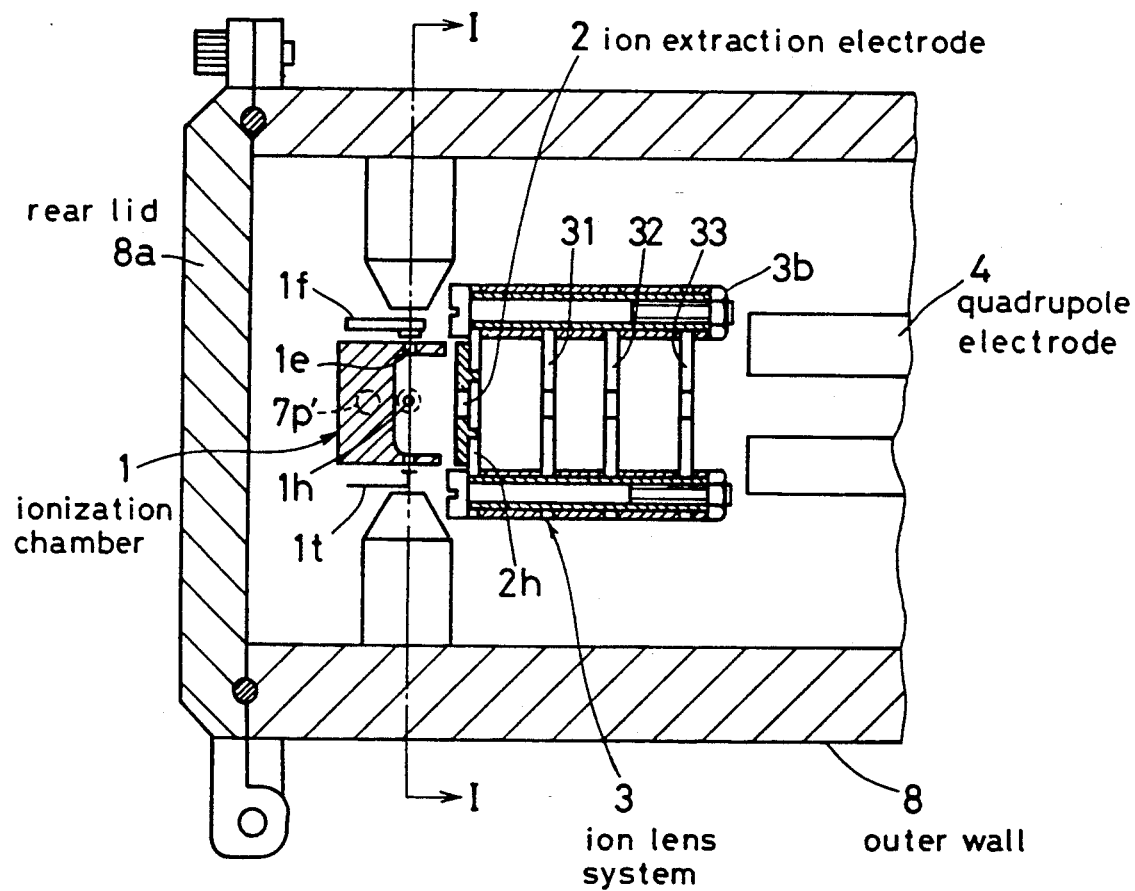
FIG. 1 shows a vertical sectional view of an ion source according a preferred embodiment of the present invention.
Figure 2:
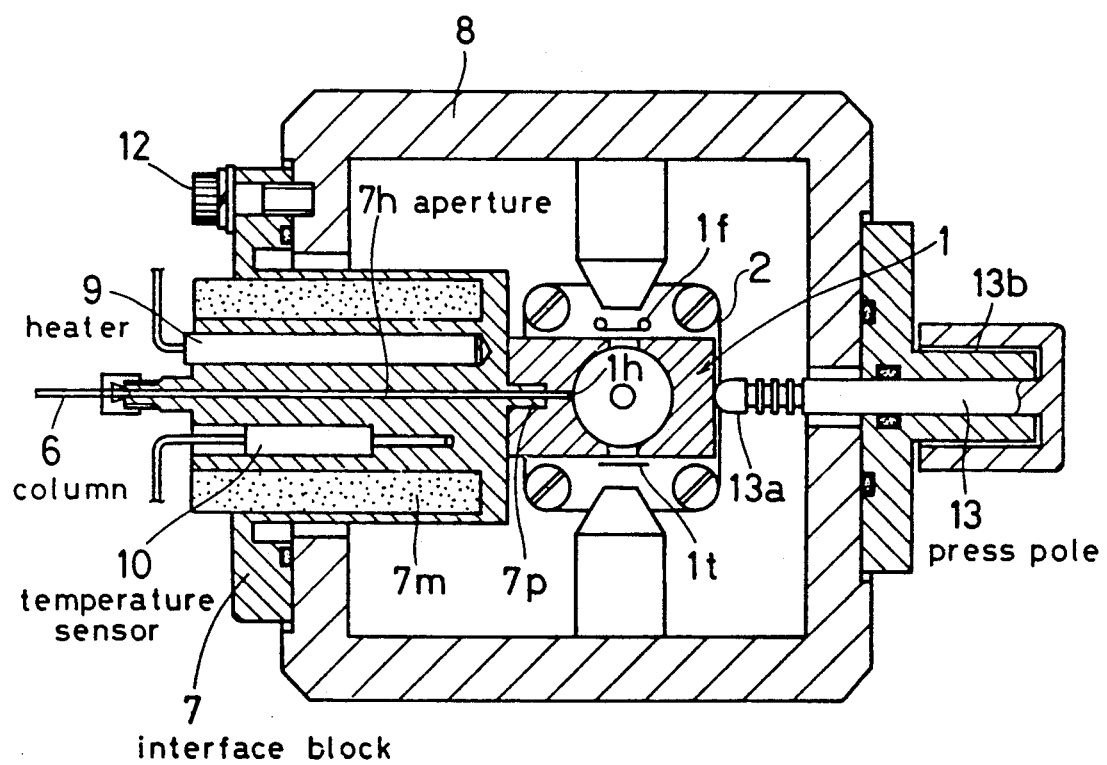
FIG. 2 shows a cross sectional view of the ion source of FIG. 1, taken along the line I—I.
Figure 3:
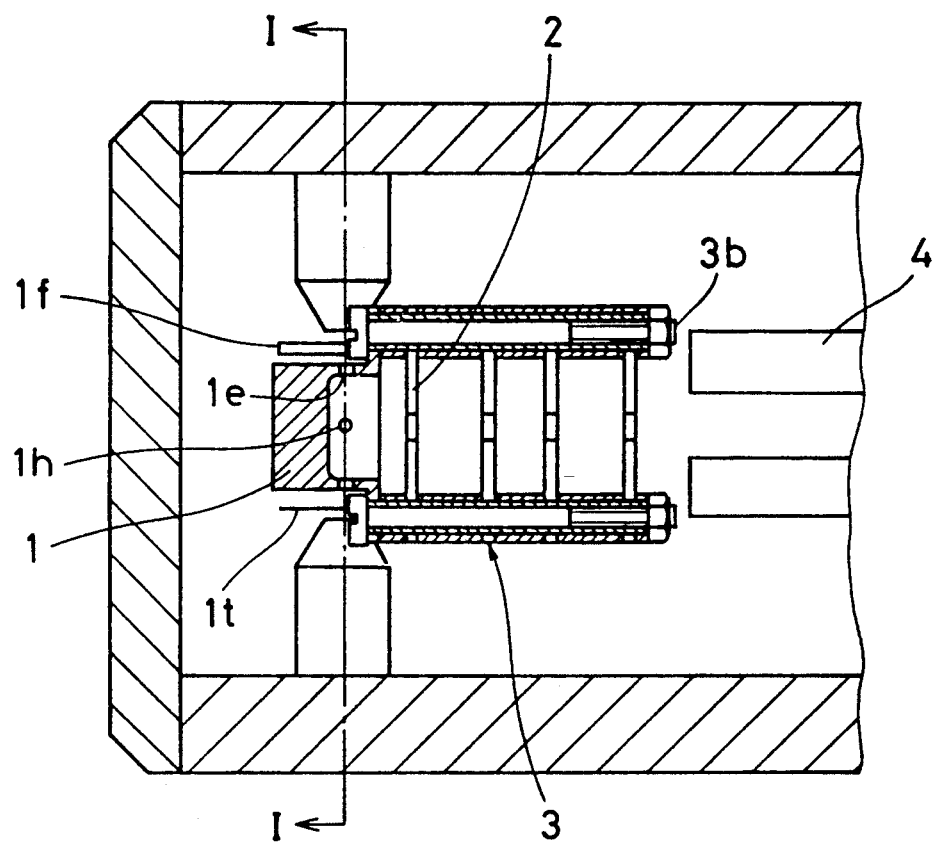
FIG. 3 shows a vertical sectional view of a conventional ion source.
Figure 4:
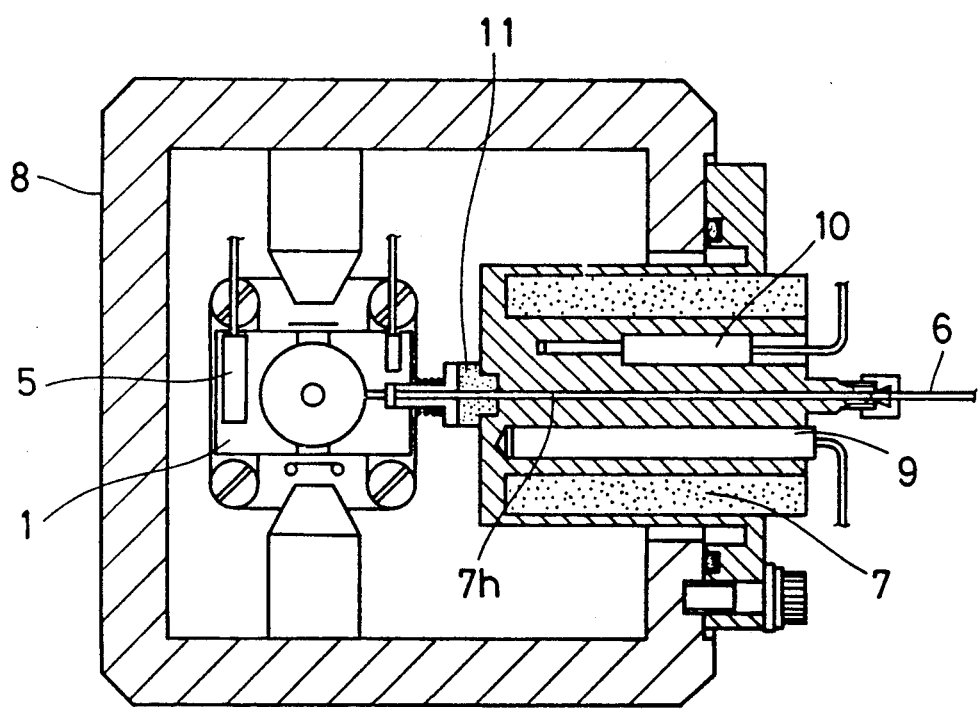
FIG. 4 shows a cross sectional view of the ion source of FIG. 3, taken along the line I—I.

FIGS. 1 and 2 show a preferred embodiment of the present invention. Referring to FIG. 1, an ionization chamber 1 is of the type for ionizing according to electron impact. Electrons emitted from a filament 1$f$ are injected into the ionization chamber 1 through an electron injection aperture 1$e$ to ionize the sample molecules introduced through a sample introduction inlet 1$h$. An electron trap 1$t$ is provided for capturing electrons passing through the ionization chamber 1. An ion source is a space covered by the ionization chamber 1 and an ion extraction electrode 2. The ion extraction electrode 2 is a part of an ion lens system 3 while the ionization chamber 1 is separated from the ion lens system 3. The ion lens system 3 is constructed such that an ion extraction electrode holder 2H and a plurality of lens electrodes 31, 32, and 33 are integrated by a bolt 3$b$ through electrically isolated spacers. A quadrupole electrode 4 is an electrode for a quadrupole type mass spectrometer.

Referring to FIG. 2, an interface block 7 is provided for connecting the ion source and a column of the gas chromatograph. The interface block 7 is attached to cover the opening on a side of an outer wall 8 of the mass spectrometer via a screw 12. Along the central axis of the interface block 7, a sample introduction aperture 7h connects to the column 6 of the gas chromatograph. A projection 7p is formed at the center of a side of the interface block 7 being within the mass spectrometer, said projection 7p being penetrated by the sample introduction aperture 7h. The projection 7p of the interface block 7 is coupled to a cavity formed around the sample introduction inlet 1h on a side of the ionization chamber 1 to thereby combine them. Since the ionization chamber 1 can rotate around the sample introduction inlet 1h and cannot be positioned only with the simple coupling by the projection 7p, there is provided another projection 7p' in line with the projection 7p so that the ionization chamber 1 is coupled with the two projections 7p and 7p' to be positioned. The projection 7p' is shown as a small circle in FIG. 1.

A press pole 13a is provided for pressing a side of the ionization chamber 1 to the inner side of the interface block 7. A thermal insulator 13a is disposed at the tip of the press pole 13. A screw 13b at the inner side of a knob is rotated for pressing the ionization chamber 1 leftward of the drawing of FIG. 2 through the press pole 13.

A heater 9 is embedded in the interface block 7, a temperature sensor 10 is provided for temperature control, and a thermal insulator 7m is positioned. Although there is no heater in the ionization chamber 1, it is directly coupled to the interface block 7 so that the ionization chamber 1 is heated by the conducting heat from the heater 9. Here, there are provided a couple of heater and temperature sensor, satisfactorily. The interface block 7 and the ionization chamber 1 are both made of stainless steel.

To clean the ion source, referring to FIGS. 1 and 2, a rear lid 8a on an outer wall 8 of the mass spectrometer is opened and the press pole 13 is returned backward. Then, the ionization chamber 1 is manually moved rightward in FIG. 2 so that the coupling of projections 7p and 7p' of the interface block 7 to the ionization chamber is released. Then, the ionization chamber 1 is outside the outer wall 8 of the mass spectrometer to clean it. Here, an ion extraction electrode 2 as a part of the ion source remains in the ion lens system 3. In this preferred embodiment the ion extraction electrode 2 is coupled to an ion extraction electrode holder 2h positioned leftmost in the ion lens system 3 in FIG. 1. The ion extraction electrode 2 is put out of the outer wall 8 of the mass spectrometer, independently on the removal of the ionization chamber 1.

According to the present invention, the ionization chamber 1 and the interface block 7 are directly in contact with each other to thereby be thermally integrated. The interface block 7 is coupled to the column 6 of the gas chromatograph, the voltage of the interface block 7 is the same as the ground voltage of the outer wall 8 of the mass spectrometer, so that the voltage of the ionization chamber 1 is the ground also. A DC bias voltage is applied to the quadrupole electrode to provide an acceleration voltage between the ionization chamber 1 and the quadrupole electrode to inject the ions to the mass spectrometer portion. Thus a DC and high frequency voltage is applied to the quadrupole electrode at the center of the DC bias voltage.

As described above, in accordance with the present invention, the cleaning of the ionization chamber can be possible by removing the ionization chamber without disassembling the ion lens system, which is very simple. Since the interface block and the ionization chamber are directly in contact with each other, the heater embedded in the interface block enables the heat of the ionization chamber via thermal conductivity. It is unnecessary to provide a specific heater or a specific temperature sensor for the ionization chamber. Here, thermal uniformity is improved with less numbers of the necessary elements and low cost. The rate of malfunction of the heater and the temperature control system becomes low. The heater is provided only in the interface block so that the break of the heater can be repaired only by changing the heater outside the vacuum. The maintenance is thus simple. While only certain embodiments of the present invention have been described, it will be apparent to those skilled in the art that various changes and modifications may be made therein without departing from the spirit and scope of the present invention as claimed.

What is claimed is:

1. An ion source for a mass spectrometer comprising:
   interface block means connected to a sample source for introducing said sample source to an ionization chamber means;
   said ionization chamber means being in direct mechanical and thermal contact with and positioned at a side of said interface block means in said mass spectrometer;
   heater means provided in said interface block means for heating both said interface block means and said ionization chamber means; and
   temperature sensor means provided in said interface block means for sensing the temperature of said interface block means and that of said ionization chamber means.

2. The ion source as set forth in claim 1, further comprising ion lens system located adjacent and independently of said ionization chamber means.

3. The ion source as set forth in claim 1, further comprising press means for pressing said ionization chamber means toward and into direct mechanical and thermal contact with said interface block means.

4. The ion source as set forth in claim 1, further comprising a gas chromatograph coupled to said mass spectrometer.

* * * * *